(12) United States Patent
Norbury et al.

(10) Patent No.: US 10,377,707 B2
(45) Date of Patent: Aug. 13, 2019

(54) PROCESS FOR THE PREPARATION OF LACTAMS FROM GLYOXALIC ACID

(71) Applicant: Conopco, Inc., Englewood Cliffs, NJ (US)

(72) Inventors: Andrew Martyn Norbury, High Peak (GB); David William Thornthwaite, Little Neston (GB)

(73) Assignee: CONOPCO INC., Englewood Cliffs, NJ (US)

( * ) Notice: Subject to any disclaimer, the term of this patent is extended or adjusted under 35 U.S.C. 154(b) by 0 days.

(21) Appl. No.: 15/750,887

(22) PCT Filed: Aug. 1, 2016

(86) PCT No.: PCT/EP2016/068287
§ 371 (c)(1),
(2) Date: Feb. 7, 2018

(87) PCT Pub. No.: WO2017/029104
PCT Pub. Date: Feb. 23, 2017

(65) Prior Publication Data
US 2018/0237388 A1 Aug. 23, 2018

(30) Foreign Application Priority Data
Aug. 20, 2015 (EP) .................... 15181849

(51) Int. Cl.
*C07D 201/08* (2006.01)
*C07D 207/38* (2006.01)
*C07D 207/44* (2006.01)

(52) U.S. Cl.
CPC ......... *C07D 201/08* (2013.01); *C07D 207/38* (2013.01); *C07D 207/44* (2013.01)

(58) Field of Classification Search
CPC ............................ C07D 201/08; C07D 207/38
See application file for complete search history.

(56) References Cited

U.S. PATENT DOCUMENTS

| | | | |
|---|---|---|---|
| 5,955,419 A | 9/1999 | Barket, Jr. et al. | |
| 8,641,948 B2 | 2/2014 | Ghogh et al. | |
| 9,527,866 B2 * | 12/2016 | Yokoo .................. | C07D 501/16 |
| 9,586,901 B2 | 3/2017 | Kumar et al. | |
| 9,930,888 B2 | 4/2018 | Parry et al. | |
| 2011/0059144 A1 | 3/2011 | Fletcher et al. | |
| 2014/0294925 A1 | 10/2014 | Yin | |
| 2015/0351393 A1 | 12/2015 | Parry et al. | |

FOREIGN PATENT DOCUMENTS

| WO | WO2006085089 | 8/2006 |
|---|---|---|
| WO | WO2007085042 | 8/2007 |
| WO | WO2010069742 | 6/2010 |
| WO | WO2014118240 | 8/2014 |

OTHER PUBLICATIONS

Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.
Guedes et al.; Solid Dispersions of Imidazolidinedione by PEG and PVP Polymers with Potential Antischistosomal Activities; PharmSciTech; Mar. 1, 2011; pp. 401-410; vol. 12, No. 1.
Chadha et al.; Analytical techniques used to characterize drug-polyvinylpyrrolidone systems in solid and liquid states—An overview; J Scientific and Industrial Research; Jun. 1, 2006; pp. 459-469; vol. 65.
Kim et al.; Solid Dispersions as a Drug Delivery System; J Pharmaceutical Investigation; Mar. 29, 2011; pp. 125-142; vol. 41, No. 3.
Carla S.M. Pereira et al., Ethyl lactate as a solvent: properties, applications and production processes—a review, Green Chemistry, 2011, pp. 2658-2671; XP055235519, vol. 13, No. 10.
IPRP in PCTEP2016069072, Aug. 2, 2017.
IPRP2 in PCTEP2016068585, Nov. 2, 2017.
IPRP2 in PCTEP2016068625, Sep. 6, 2017.
Mary E. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Search Report and Written Opinion in PCTEP2016067616, dated Sep. 12, 2016.
Search Report and Written Opinion in PCTEP2016068008, dated Sep. 12, 2016.
Search Report and Written Opinion in PCTEP2016068010, dated Sep. 12, 2016.
Search Report and Written Opinion in PCTEP2016068287, dated Oct. 26, 2016.
Search Report and Written Opinion in PCTEP2016068585, dated Oct. 4, 2016.
Search Report and Written Opinion in PCTEP2016068625, dated Sep. 9, 2016.
Search Report in EP15181842, dated Dec. 10, 2015.
Search Report in EP15181846, dated Dec. 11, 2015.
Search Report in EP15181847, dated Dec. 17, 2015.
Search Report in EP15181851, dated Dec. 11, 2015.
Search Report in EP15181856, dated Dec. 14, 2015.

(Continued)

*Primary Examiner* — Golam M Shameem
(74) *Attorney, Agent, or Firm* — Foley & Lardner LLP

(57) ABSTRACT

A process for the synthesis of lactams suitable for use in antimicrobial, anti-biofilm bacteriostatic compositions.

11 Claims, No Drawings

(56) References Cited

OTHER PUBLICATIONS

Search Report in EP15181858, dated Dec. 11, 2015.
Von R. Scheffold und P. Dubs, Synthese von Azaprotoanemoninen, Helvetica Chimica Acta, 1967, pp. 798-808; XP55249911.
Written Opinin in EP15181856, dated Dec. 14, 2015.
Written Opinion 2 in PCTEP2016067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.

* cited by examiner

PROCESS FOR THE PREPARATION OF LACTAMS FROM GLYOXALIC ACID

This application claims priority from EP 15181849.9 filed 20 Aug. 2015 which is herein incorporated by reference for all purposes.

The present invention relates to processes for the synthesis of lactams. The lactams are suitable for use in antimicrobial, anti-biofilm and bacteriostatic compositions.

WO 2007/085042 and WO 2004/016588 disclose lactams for antimicrobial benefit and steps towards their synthesis.

Scheffold et al. (Helv. Chem. Acta, 1967, No. 79 pp. 798-808) also describes methods for the synthesis of lactones and lactams.

Despite these methods, there is a need for further methods for the synthesis of lactams. In particular, owing to the usefulness of lactams in antimicrobial compositions, there is a need for improved methods for synthesis to facilitate production of lactams on a commercial scale.

The present invention relates to improved methods for the synthesis of lactams for use in an antimicrobial composition.

In a first aspect, the present invention may provide a process for the synthesis of a lactam, the process comprising the steps of:
(a) an Aldol condensation between an acetone initiator and glyoxalic acid;
(b) treating the product(s) of step (a) with an organic acid to effect dehydration;
(c) reacting the product of step (b) with ammonia or a primary amine, or salt thereof, to afford a lactam.

It will appreciated that starting materials, products and reagents may be used, where appropriate, as salts, hydrates and solvents thereof. Suitably, the glyoxalic acid is provided as the glyoxalic acid monohydrate.

Step (a) is an Aldol condensation. In other words, it is the reaction of two carbonyl containing compounds (the acetone initiator and the glyoxalic acid) to generate a β-hydroxy carbonyl compound that then dehydrates to give an α,β-unsaturated carbonyl compound. It may be thought of as an Aldol addition followed by dehydration.

In the reaction of step (a), this α,β-unsaturated carbonyl compound (product [A]) can then undergo cyclisation as shown below to give a lactone (product [B]) (substituents chosen for clarity, and not by way of limitation).

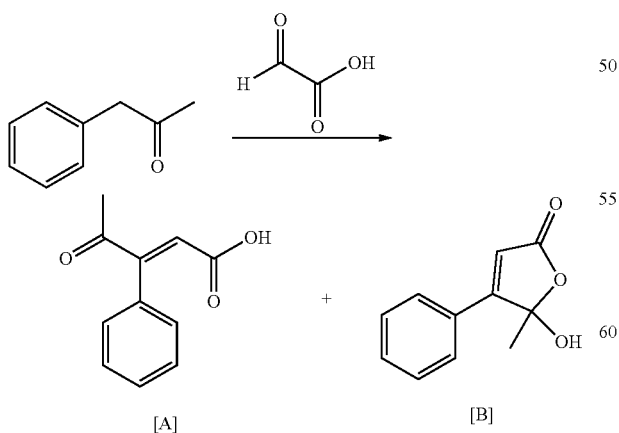

It will be appreciated that the ratio of [A] to [B] will depend on reaction conditions, but a mixture is typically obtained (with [A] as the major product, and [B] as the minor product). Of course, both [A] and [B] may be used separately.

The methods of the prior art use only [B] (the minor product) in subsequent steps. The present inventor(s) have found that it is not necessary to separate [A] and [B] to synthesise a lactam. Instead, the inventor(s) have found that, by using step (b) as claimed, both [A] and [B] can be used without separation.

Step (a) may be acid catalysed. In other words, step (a) may be an Aldol condensation between an acetone initiator and glyoxalic acid in the presence of an acid such as phosphoric acid ($H_3PO_4$) or an anhydride thereof (for example, $P_2O_5$).

The term "acetone initiator" as used herein refers to a compound having an acetone moiety. It may be substituted. Suitably, the acetone initiator is a compound of formula Ia:

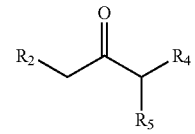

wherein $R_2$, $R_4$, and $R_5$ are as defined herein with respect to Formula I and II or any subset herein defined.

For example, $R_2$ may be aryl or aralalkyl. Preferably, $R_2$ is an optionally substituted phenyl group, for example, an unsubstituted phenyl or mono-substituted phenyl group. Preferred substituents include halogen and methyl. For example, and without limitation, $R_2$ may be selected from phenyl, 4-fluorophenyl, 4-chlorophenyl, 4-bromophenyl and 4-methylphenyl.

Preferably, $R_4$ is H. Preferably, $R_5$ is H.

Accordingly, in some cases the acetone initiator is a 1-phenylpropan-2-one. For example, and without limitation, the acetone initiator may be 1-phenylpropan-2-one, 1-(4'fluorophenyl)propan-2-one, 1-(4'chlorophenyl)propan-2-one, 1-(4'bromophenyl)propan-2-one or 1-(4-tolyl)propan-2-one.

Step (b) is a dehydration reaction, as shown:

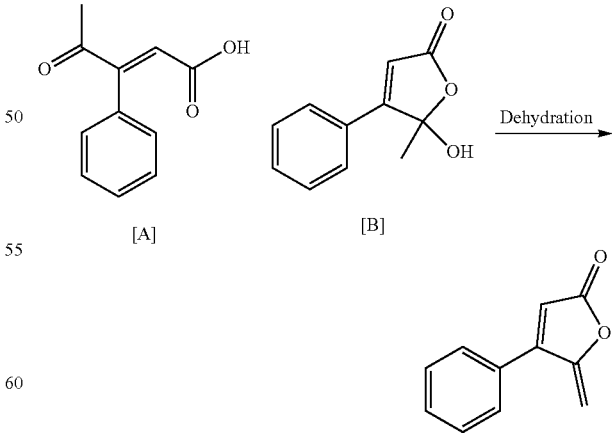

The product of step (a) is treated with an organic acid. Suitably, the organic acid is a sulfonic acid. Suitably, the organic acid has a $pK_a$ of 0 or less. For example, the organic acid may be para-toluenesulfonic acid (pTSA; TsOH) or methylsulfonic acid (MsOH). pTSA is a solid, and so may be useful in syntheses in which solid reagents are preferred (for handling or similar). MsOH is a liquid, so may be preferable for use on a production scale.

Suitably, water is removed during step (b). Methods for water removal are known in the art and include Dean-Stark apparatus, soxhelet use and molecular sieves on a laboratory scale.

The inventor(s) have found that step (c) can be performed using this exo-methylene lactone to give lactams. Advantageously, this avoids the use of 5-chloro-5-methylfuran-2-ones (as are used in known methods), which may be unsafe for use on production scale.

Step (c) uses ammonia or a primary amine (in other words, an amine of formula $HNR_3$, where $R_3$ is as defined herein). Step (c) may be performed in an alcoholic solution, for example in methanol. Other solvents may be present. For example, step (c) may be performed in a mixture of DCM and methanol. Where $R_3$ is H (i.e. ammonia is used), the inventor(s) have found that a concentrated aqueous solution of ammonia may be used. A water-miscible co-solvent, for example a THF such as 2-methyltetrahydrofuran, may be added. A salt of said ammonia or primary amine may also be used, for example, the ammonia or primary amine may be provided as a solution in acetic acid (in which proton transfer will occur).

The lactam produced in step (c) is a 5-hydroxy-5-methyl-1H-pyrrol-2-one. Lactams having this structure are useful in antimicrobial compositions. However, the corresponding dehydrated products, that is, a 5-methylene-1H-pyrrol-2-one structure, are also useful in antimicrobial compositions.

Accordingly, the process may further comprise a step (d) which is dehydration of the lactam product of step (c) to afford a lactam having an exo-methylene group.

Suitably, the reagent used in step (d) is boron trifluoride etherate. The reaction may be carried out in DCM, although other suitable solvents will be envisaged. The inventor(s) observed that use of boron trifluoride etherate afforded product cleanly and, advantageously, did not lead to the formation of unwanted polymerisation by-products. Of course, it will be appreciated that other reagents can be used. For example, and not by way of limitation, the inventor(s) have demonstrated dehydration using phosphorus pentoxide in DCM and copper sulfate in THF.

In some case, the lactam produced is a lactam of formula (I) or (II):

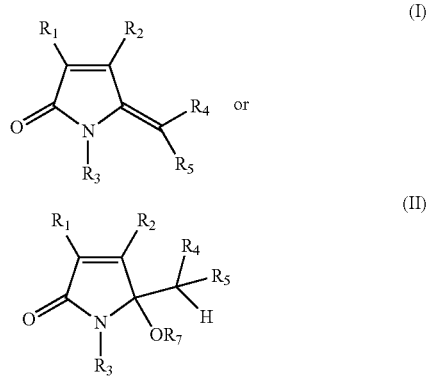

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and $-C(O)CR_6=CH2$;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and $-C(O)CR_6=CH_2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl; and Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

It will be appreciated that $R_3$ may be introduced through use of a primary amine of formula $HNR_3$ or, where $R_3$ is not H, through subsequent alkylation or similar of the pyrrolone. Accordingly, in some embodiments, the process comprises step (e), which may follow step (c), step (d), or step (f) (below), wherein the product of step (c), step (d) or step (f) is reacted with a compound of formula $R^3$-LG, wherein LG is a leaving group, for example, a halogen such as chloride or a OMs group. A base such as sodium methoxide may be present.

It will be appreciated that $R_7$ is selected from hydrogen and $-C(O)CR_6=CH_2$. In some cases, $R_7$ is hydrogen. In some cases $R_7$ is $-C(O)CR_6=CH_2$. In some cases $R_3$ is $-C(O)CR_6=CH_2$. In these latter two cases, the process may include a further step (f). Step (f) may follow step (c), step (d) or step (e) as appropriate.

Step (f), if present, comprises treating the product of step (c), step (d) or step (e) with an acryloyl chloride, for example, where $R_6$ is methyl, the acryloyl chloride is methacryloyl chloride.

Suitably, the reaction is performed dropwise in an inert solvent, for example, DCM at less than 5° C.

Certain exemplary lactams may include those disclosed in WO 2007/085042 and WO 2004/016588, the contents of which, and in particular the lactam structures explicitly drawn out therein, are incorporated by reference.

Preferred lactams may include:

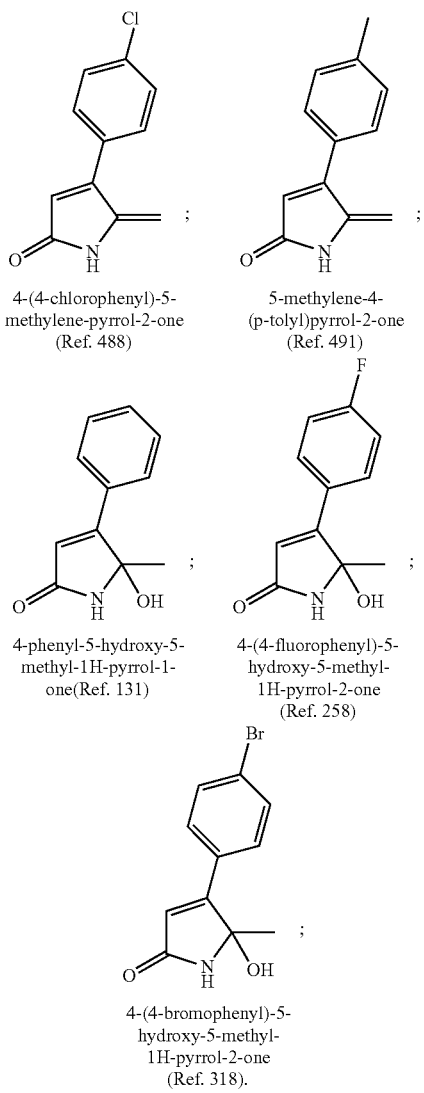

4-(4-chlorophenyl)-5-methylene-pyrrol-2-one (Ref. 488)

5-methylene-4-(p-tolyl)pyrrol-2-one (Ref. 491)

4-phenyl-5-hydroxy-5-methyl-1H-pyrrol-1-one(Ref. 131)

4-(4-fluorophenyl)-5-hydroxy-5-methyl-1H-pyrrol-2-one (Ref. 258)

4-(4-bromophenyl)-5-hydroxy-5-methyl-1H-pyrrol-2-one (Ref. 318).

The acetone initiator may be commercially available. Where an acetone initiator is not commercially available, the following synthesis may be used. For both commercially available and non-commercially available acetone initiators, the invention may provide a process for making an acetone initiator, the process comprising:

(i) reacting an aldehyde with nitroethane; and
(ii) treating the product of step (i) with a Lewis acid.

This process may be combined with the process of the first aspect, before step (a).

For example, step (i) may comprise reaction of an optionally substituted benzaldehyde with nitroethane.

Suitably, step (i) is performed in refluxing ammonium acetate and acetic acid.

For step (ii), iron powder and iron trichloride may be used.

DESCRIPTION

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

The compositions may also be used as additive compositions; in other words, the composition may be combined with further ingredients such as excipients to form a composition as described above.

EXAMPLES

The following syntheses are provided by way of illustration and exemplification, and not by way of limitation.

Synthesis of 1-bromo-4-(2-nitroprop-1-en-1-yl)benzene (2054548)

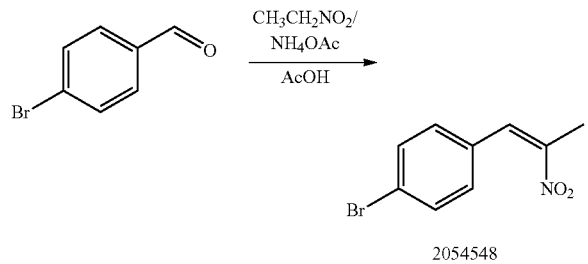

A mixture of 4-bromobenzaldehyde (250 g, 1.35 mol), nitroethane (101 g, 1.35 mol), ammonium acetate (104 g, 1.35 mol) and acetic acid (1 lt) was heated at reflux for fourteen hours and allowed to cool. After filtering, water (2 lt) was added and the resultant precipitate collected by filtration and then washed with water. Recrystallisation from isopropanol gave 1-bromo-4-(2-nitroprop-1-en-1-yl)benzene (2054558) as a yellow solid (130 g (40%), Rf=0.5 (1:9 ethyl acetate:heptane); Mp=88-90° C.).

Synthesis of 2-(4-bromophenyl)acetone (2044550)

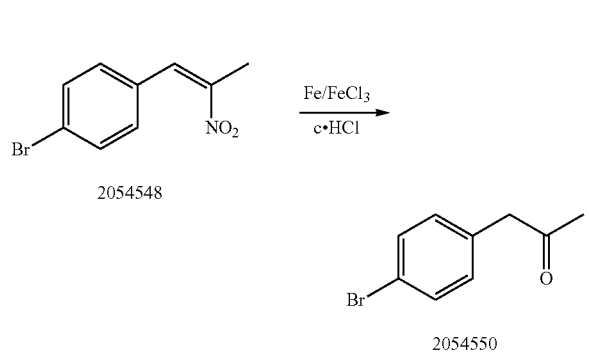

A mixture of 1-bromo-4-(2-nitroprop-1-en-1-yl)benzene (116.8 g, 0.48 mol), iron powder (228 g, 4.08 mol) and iron (III) chloride (2.28 g, 14 mmol) in water (456 ml) was warmed to 65° C. and 37% hydrochloric acid (ca. 20 ml) added dropwise. Heating was stopped and the mixture slowly exothermed to ca. 95° C. Once the exotherm had subsided, further 37% HCl (ca. 200 ml) was slowly added and the mixture left to stir to room temperature. Ethyl acetate (900 ml) was then added and the mixture stirred for 30 min. It was then filtered through a pad of celite and the layers separated; the aqueous was extracted with further ethyl acetate (200 ml) and the combined organics washed with brine and dried over magnesium sulphate. After filteration and concentrated to give 2-(4-bromophenyl)acetone (2044550) as an oil (96.5 g (94%)) which was pure enough to use in the following step.

Synthesis of 1-fluoro-2-(2-nitroprop-1-en-1-yl)benzene (2054547)

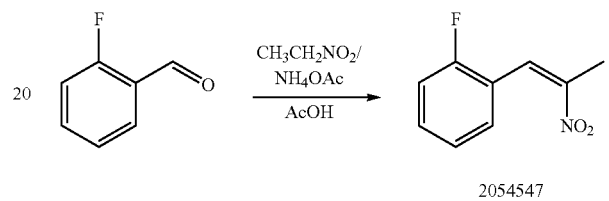

A mixture of 2-fluorobenzaldehyde (250 g, 2.01 mol), nitroethane (151 g, 2.01 mol), ammonium acetate (155 g, 2.01 mol) and acetic acid (1 lt) was heated at reflux for fourteen hours and allowed to cool. After filtering, water (3 lt) was added and the mixture extracted with ethyl acetate (1 lt). The layers were separated and the organic washed with water (3×500 ml) then saturated sodium bicarbonate solution (2×500 ml). After drying, concentration gave an oil which was purified by reduced pressure distillation to give 1-fluoro-2-(2-nitroprop-1-en-1-yl)benzene (2054547) (160 g (44%), Rf=0.75 (1:4 ethyl acetate:heptane), Bp=90-100° C. @ 0.5-1.0 mmHg).

Synthesis of 1-(2-fluorophenyl)propan-2-one (2054549)

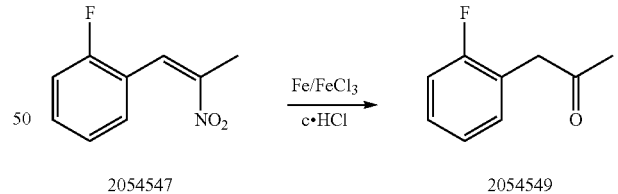

A suspension of 1-fluoro-2-(2-nitroprop-1-en-1-yl)benzene (2054547) (160 g, 0.88 mol), iron powder (320 g, 5.71 mol) and iron (III) chloride (3.2 g, 19.6 mmol) in water (640 ml) was heated to 80° C. with overhead stirring and 37% hydrochloric acid (320 ml) added over twenty minutes. The reaction was then heated to reflux for an hour and allowed to cool. Ethyl acetate (1 lt) was added and the mixture filtered through a pad of celite; the layers were separated and the organic dried and concentrated. The oil obtained was purified by reduced pressure distillation to give 1-(2-fluorophenyl)propan-2-one (2054549) (90 g (67%), Rf=0.40 (1:4 Ethyl acetate:heptanes), Bp=70° C. @ 1 mm Hg).

Synthesis of 4-(4-bromophenyl)-5-methylene-1H-pyrrol-2(5H)-one (2053466)

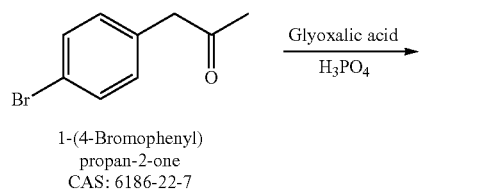

1-(4-Bromophenyl)
propan-2-one
CAS: 6186-22-7

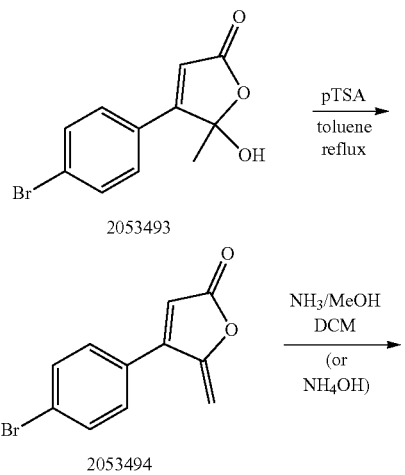

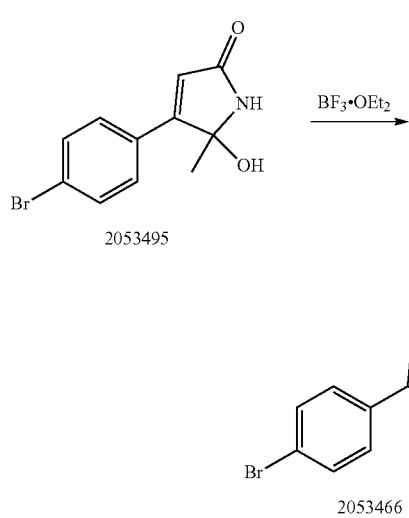

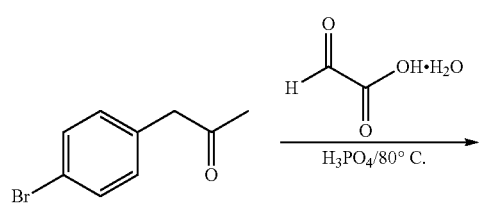

Synthesis of 4-(4-bromophenyl)-5-hydroxy-5-methylfuran-2(5H)-one (2053493)

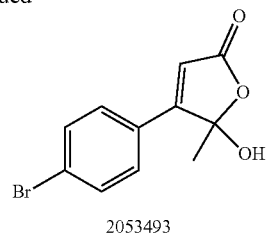

To a stirred mixture of 1-(4-bromophenyl)propan-2-one (29.4 g, 0.137 mol) in phosphoric acid (44 ml, 0.68 mol) was added glyoxylic acid monohydrate (19.05 g, 0.21 mol) and the reaction heated to 80-85° C. overnight which resulted in the formation of a dark solid. This was broken up manually and then the reaction contents poured into a two phase mixture of water (400 ml) and ethyl acetate (600 ml). After stirring until both layers were clear and there was no un-dissolved solid, the layers were separated and the aqueous layer extracted further with ethyl acetate (100 ml). The combined organics were washed with water (3×200 ml), saturated sodium bicarbonate solution (200 ml), brine (100 ml) and then dried and concentrated to give 4-(4-bromophenyl)-5-hydroxy-5-methylfuran-2(5H)-one (2053493) as a solid which was clean enough to use in the next reaction (29 g, 78%). $^1$H NMR (400 MHz, MeOH-d3): δ 7.66 (4H dd), 6.4 (1H, s), 1.88 (3H, s).

Synthesis of 4-(4-bromophenyl)-5-methylenefuran-2(5H)-one (2053494)

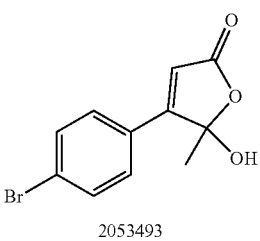 

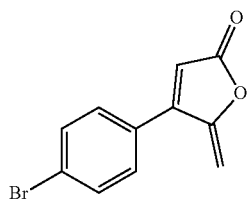

To 4-(4-bromophenyl)-5-hydroxy-5-methylfuran-2(5H)-one (2053493) (30 g, 0.11 mol) stirred in toluene (1 L) was added p-toluenesulfonic acid monohydrate (23.3 g, 0.12 mol) and the reaction heated under a Dean-Stark apparatus for 4 hrs. The reaction mixture was then concentrated to an oil and partitioned between ethyl acetate (600 ml) and saturated sodium bicarbonate solution (400 ml) and stirred for 15 min. The layers were separated and the organics washed with further saturated sodium bicarbonate solution (200 ml). The organics were then washed with brine (100 ml), dried and concentrated to a solid (28 g, crude) which was recrystallised from isopropanol (150 ml) giving 4-(4-bromophenyl)-5-methylenefuran-2(5H)-one (2053494) (22.9 g) which was 97% pure by LC. The mother liquors were concentrated and chromatographed eluting with 5:1 heptane/ethyl acetate to give further product (3.6 g). This gave a combined yield of (22.9 g, 82%). $^1$H NMR (300 MHz, CHCl$_3$-d3): δ 7.66 (2H, d), 7.35 (2H, d), 6.28 (1H, s), 5.39 (1H, d), 5.0 (1H, d).

Synthesis of 4-(4-bromophenyl)-5-hydroxy-5-methyl-1H-pyrrol-2(5H)-one (2053495)

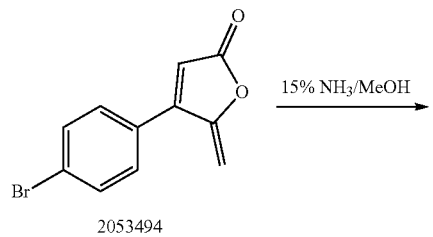

2053494

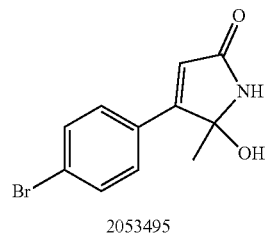

2053495

A mixture of 4-(4-bromophenyl)-5-methylenefuran-2(5H)-one (2053494) (22.9 g, 0.09 mol) in ammonia/methanol solution (220 ml, ca 15% w/w) was stirred at room temperature overnight. The reaction was concentrated to a gummy tan solid which was then stirred in hot ethyl acetate (100 ml) until a fine free flowing solid was obtained. The liquor was allowed to cool to room temp before filtering off the solid and drying on the drying tray to give 4-(4-bromophenyl)-5-hydroxy-5-methyl-1H-pyrrol-2(5H)-one (2053495) as a yellow solid, (17.3 g, 71%). $^1$H NMR (400 MHz, CHCl$_3$-d3): δ 7.66 (2H, d), 7.53 (2H, d), 6.12 (1H, s), 1.63 (3H, s).

Alternative Procedure 4-(4-Bromophenyl)-5-methylenefuran-2(5H)-one (2053494) (40 g, 0.16 mol) was stirred in conc. aqueous ammonia (400 ml, ca 14 M soln) for 24 hrs. Tlc (1:1 ethyl acetate/heptane) showed some of the furanone still remained. A further portion of conc. ammonia was therefore added (100 ml) and the reaction stirred for a further 24 hrs. Water (500 ml) and ethyl acetate (1 L) were then added and the mixture stirred for 15 min. The layers were separated and the aqueous layer extracted with ethyl acetate (2×400 ml). The combined organics were washed with brine (400 ml) and dried with sodium sulfate before filtering and concentrating to give 4-(4-bromophenyl)-5-hydroxy-5-methyl-1H-pyrrol-2(5H)-one (2053495) as a yellow solid, (36.8 g, 85%).

Synthesis of 4-(4-bromophenyl)-5-methylene-1H-pyrrol-2(5H)-one (2053466)

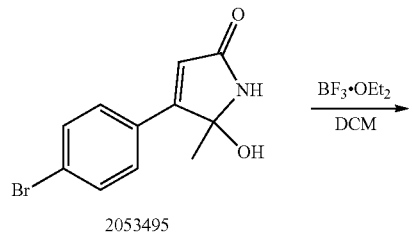

2053495

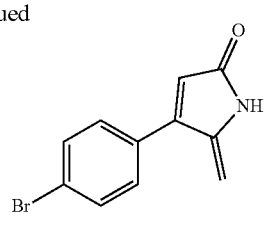

2053466

To a stirred suspension of 4-(4-bromophenyl)-5-hydroxy-5-methyl-1H-pyrrol-2(5H)-one (2053495) (17.2 g, 0.064 mol) in dichloromethane (400 ml) at room temperature under argon was added boron trifluoride etherate (13.6 g, 0.096 mol) dropwise over ca. 10 min. The reaction was left to stir for 1 hr and was then poured into a mixture of water (440 ml) and dichloromethane (200 ml). The biphasic mixture was stirred for 30 min; as there were still some solids present, the mixture was warmed to ca 40° C. to try and aid dissolution. The layers were then separated and the aqueous extracted further with dichloromethane (2×150 ml); the combined organics were dried and concentrated to a solid. This was then refluxed in a 2:1 mixture of ethyl acetate/heptane (75 ml) for 15 min before being cooled to room temperature, filtered washed with the same cold solvent mixture and dried on the drying tray to give 4-(4-bromophenyl)-5-methylene-1H-pyrrol-2(5H)-one (2053466) as a yellow solid (12 g, 75%>99% pure by LC). $^1$H NMR (300 MHz, CHCl$_3$-d3): δ 8.2 (1H br s), 7.60 (2H, d), 7.57 (2H, d), 6.23 (1H, s), 5.14 (1H, d), 4.9 (1H, d).

Synthesis of 4-(2-fluorophenyl)-5-hydroxy-5-methylfuran-2(5H)-one (2053496)

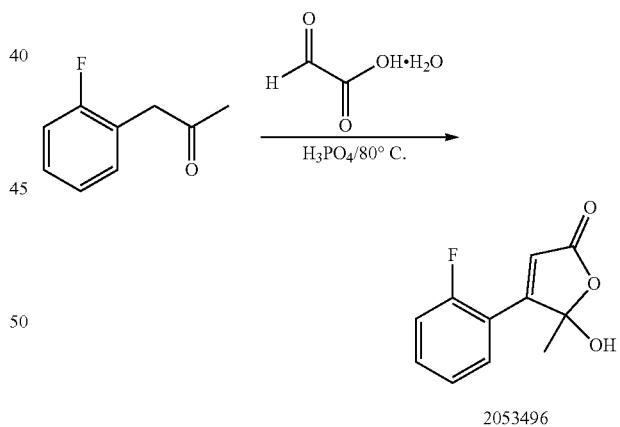

2053496

To a stirred mixture of 1-(2-fluorophenyl)propan-2-one (62.17 g, 0.41 mol) in phosphoric acid (139 ml, 2.05 mol) was added glyoxylic acid monohydrate (56.41 g, 0.61 mol) and the reaction heated to 80-85° C. overnight. The reaction was allowed to cool and was poured into a two phase mixture of ethyl acetate (1 L) and water (500 ml); this mixture was stirred until a solution was obtained. The layers were separated and the organics washed with water (500 ml), saturated sodium bicarbonate solution (2×300 ml) and brine (100 ml) before being dried and concentrated to give 4-(2-fluorophenyl)-5-hydroxy-5-methylfuran-2(5H)-one (2053496) as a solid which was clean enough to use directly in the next reaction, (38.36 g, 45%). $^1$H NMR (400 MHz, MeOH-d3): δ 8.0 (1H td), 7.28 (1H, m), 7.3 (3H, m) 6.5 (1H, s) 1.81 (3H, s).

Synthesis of 4-(2-fluorophenyl)-5-methylenefuran-2(5H)-one (2053497)

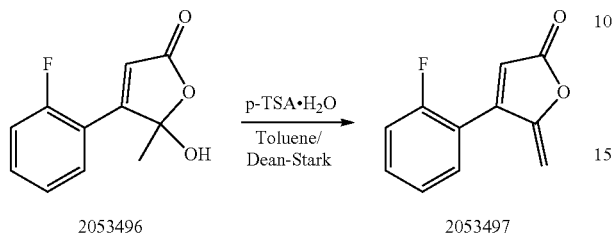

2053496 → 2053497

To 4-(2-fluorophenyl)-5-hydroxy-5-methylfuran-2(5H)-one (2053496) (38.2 g, 0.18 mol) stirred in toluene (1 L) was added p-toluenesulfonic acid monohydrate (38.4 g, 0.20 mol) and the reaction heated under a Dean-Stark apparatus for ca 4-5 hrs. The reaction was then allowed to cool and was concentrated to an oil which was poured into ethyl acetate (600 ml) and saturated sodium bicarbonate solution (400 ml) and stirred for 15 min. The layers were then separated and the organics washed with further saturated sodium bicarbonate solution (200 ml) and then brine (200 ml); after drying, removal of the solvent under reduced pressure gave an oil which crystallised on cooling to give 4-(2-fluorophenyl)-5-methylenefuran-2(5H)-one (2053497) as an orange solid, (36.9 g, 100% crude). NB this was used directly in the following reaction. $^1$H NMR (300 MHz, CDCl3-d): δ 7.6-7.4 (2H m), 7.4-7.2 (3H, m), 6.4 (1H, s), 5.38 (1H, d), 5.0 (1H, d).

Synthesis of 4-(2-fluorophenyl)-5-hydroxy-5-methyl-1H-pyrrol-2(5H)-one (2053498)

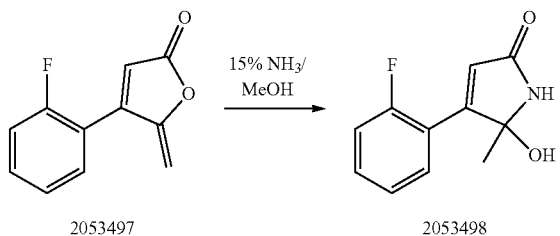

2053497 → 2053498

A mixture of 4-(2-fluorophenyl)-5-methylenefuran-2(5H)-one (2053497) (36.9 g, 0.194 mol) was stirred in ammonia/methanol solution (460 ml, ca 15% w/w) at room temperature overnight. The reaction was concentrated to a gummy/foamy solid; this was triturated with hot ether (300 ml, with heating) which resulted in a free flowing solid. The solid was collected by filtration, washed with a little cold ether and then air-dried to 4-(2-fluorophenyl)-5-hydroxy-5-methyl-1H-pyrrol-2(5H)-one (2053498) as a tan solid, (29.5 g, 73%). $^1$H NMR (400 MHz, MeOH-d3): δ 8.06 (1H td), 7.4 (1H, m), 7.2 (3H, m) 6.7 (1H, s), 6.4 (1H, s), 1.76 (3H, s).

Alternative Procedure 4-(2-Fluorophenyl)-5-methylenefuran-2(5H)-one (2053497) (17.4 g, 0.091 mol) was stirred in conc. aqueous ammonia (200 ml, ca 14 M soln) and the reaction left to stir for 24 hrs. Tlc (1:1 ethyl acetate/heptane) showed complete reaction. Water (200 ml) and ethyl acetate (400 ml) were added and the mixture stirred for 15 min. The layers were then separated and the aqueous further extracted with ethyl acetate (3×250 ml). The combined organics were washed with brine (200 ml), dried with sodium sulfate, filtered and concentrated to give 4-(2-fluorophenyl)-5-hydroxy-5-methyl-1H-pyrrol-2(5H)-one (2053498) as an orange solid, (13.55 g, 72%).

Synthesis of 4-(2-fluorophenyl)-5-methylene-1H-pyrrol-2(5H)-one (2053467)

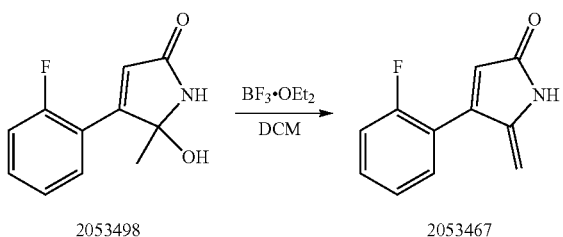

2053498 → 2053467

To a stirred suspension of 4-(2-fluorophenyl)-5-hydroxy-5-methyl-1H-pyrrol-2(5H)-one (2053498) (0.495 g, 2.4 mmol) in dichloromethane (20 ml) cooled to 0° C. was added dropwise boron trifluoride etherate (0.5 ml, 3.6 mmol). The resultant solution was stirred to room temperature over an hour and then the solvent was removed under reduced pressure. The residue was redissolved in dichloromethane (50 ml) and washed with water (20 ml) and then brine (20 ml); after drying, the solvent was removed under reduced pressure. The solid thus obtained was purified by passing through a plug of silica using dichloromethane as eluent giving 4-(2-fluorophenyl)-5-methylene-1H-pyrrol-2(5H)-one (2053467) as a brown solid (0.276 g, 61%). $^1$H NMR (300 MHz, CDCl3-d): δ 8.34 (1H br s), 7.3-7.2 (3H m), 7.5-7.35 (2H, m), 6.33 (1H, s), 5.14 (1H, d), 4.9 (1H, s).

It will be appreciated that, except where expressly provided otherwise, all preferences are combinable.

The invention claimed is:

1. A process for the synthesis of a γ-lactam, the process comprising the steps of:
   (a) performing an Aldol condensation between an acetone initiator and glyoxalic acid;
   (b) treating the product(s) of step (a) with an organic acid to effect dehydration;
   (c) reacting the product of step (b) with ammonia or a primary amine, or salt thereof, to afford the γ-lactam.

2. The process of claim 1, wherein the organic acid of step (b) is a sulfonic acid, optionally wherein the sulfonic acid is para-toluenesulfonic acid or methylsulfonic acid.

3. The process of claim 1, wherein step (c) uses ammonia, optionally wherein step (c) uses concentrated aqueous ammonia.

4. The process of claim 1, wherein the process further comprises:
   (d) dehydration of the γ-lactam product of step (c) to afford a γ-lactam having an exo-methylene group.

5. The process of claim 4, wherein step (d) uses boron trifluoride etherate.

6. The process of claim 1, wherein process further comprises making the acetone initiator before step (a), the process comprising the steps of:

(i) reacting an aldehyde with nitroethane; and (ii) treating the product of step (i) with a Lewis acid;

optionally wherein Lewis acid is Fe/FeCl$_3$.

7. The process of claim 1, wherein the γ-lactam is a lactam of formula (I) or (II):

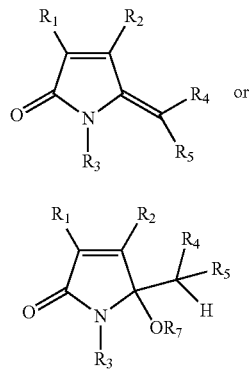

wherein:

R$_1$ and R$_2$ are each independently selected from hydrogen, halogen, alkyl, cycloalkyl, alkoxy, oxoalkyl, alkenyl, heterocyclyl, heteroaryl, aryl and aralalkyl; and R$_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;

R$_4$ and R$_5$ are independently selected from hydrogen, aryl, heterocyclyl, heteroaryl, and arylalkyl; and R$_6$ is selected from hydrogen and methyl; and R$_7$ is selected from hydrogen and —C(O)CR$_6$=CH$_2$.

8. The process of claim 7, wherein;

R$_1$ is hydrogen;

R$_3$ is hydrogen;

R$_4$ is hydrogen;

R$_5$ is hydrogen;

R$_6$ is hydrogen;

R$_7$ is hydrogen; and R$_2$ is aryl or aralalkyl.

9. The process of claim 7, wherein R$_2$ is a phenyl group or a substituted phenyl group, optionally wherein R$_2$ is a mono-substituted phenyl group.

10. The process of claim 9, wherein R$_2$ is selected from phenyl, 4-fluorophenyl, 4-chlorophenyl, 4-bromophenyl and 4-methylphenyl.

11. The process of claim 1, wherein the γ-lactam is a lactam selected from:

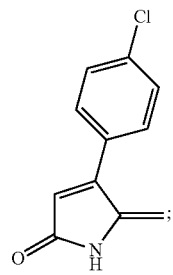 (Ref. 488)

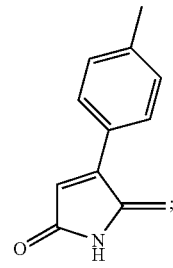 (Ref. 491)

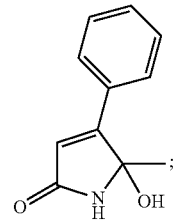 (Ref. 131)

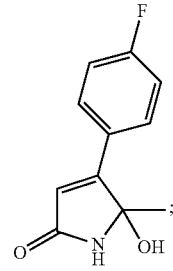 (Ref. 258)

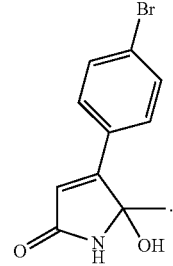 (Ref. 318)

* * * * *